United States Patent
Perez-Prat Vinuesa et al.

(10) Patent No.: US 7,629,158 B2
(45) Date of Patent: Dec. 8, 2009

(54) CLEANING AND/OR TREATMENT COMPOSITIONS

(75) Inventors: Eva Maria Perez-Prat Vinuesa, Newcastle upon Tyne (GB); Colin Ure, Newcastle upon Tyne (GB); Andre Cesar Baeck, Bonheiden (BE); Philip Frank Souter, Morpeth (GB)

(73) Assignee: The Procter & Gamble Company, Cincinnati, OH (US)

( * ) Notice: Subject to any disclaimer, the term of this patent is extended or adjusted under 35 U.S.C. 154(b) by 49 days.

(21) Appl. No.: 11/811,129

(22) Filed: Jun. 8, 2007

(65) Prior Publication Data
US 2008/0005851 A1 Jan. 10, 2008

Related U.S. Application Data

(60) Provisional application No. 60/814,442, filed on Jun. 16, 2006.

(51) Int. Cl.
*C12N 9/00* (2006.01)
*C12N 9/26* (2006.01)
*C07H 21/04* (2006.01)

(52) U.S. Cl. ........................ 435/201; 435/183; 536/23.2

(58) Field of Classification Search ........................ None
See application file for complete search history.

(56) References Cited

U.S. PATENT DOCUMENTS

| | | | |
|---|---|---|---|
| 4,430,243 A | 2/1984 | Bragg | |
| 4,597,898 A | 7/1986 | Vander Meer | |
| 4,760,025 A | 7/1988 | Estell et al. | |
| 4,762,636 A | 8/1988 | Balliello et al. | |
| 4,990,280 A | 2/1991 | Thorengaard et al. | |
| 5,188,937 A | 2/1993 | Schulte et al. | |
| 5,486,303 A | 1/1996 | Capeci et al. | |
| 5,489,392 A | 2/1996 | Capeci et al. | |
| 5,516,448 A | 5/1996 | Capeci et al. | |
| 5,565,422 A | 10/1996 | Del Greco et al. | |
| 5,569,645 A | 10/1996 | Dinniwell et al. | |
| 5,574,005 A | 11/1996 | Welch et al. | |
| 5,576,282 A | 11/1996 | Miracle et al. | |
| 5,595,967 A | 1/1997 | Miracle et al. | |
| 5,597,936 A | 1/1997 | Perkins et al. | |
| 5,679,630 A | 10/1997 | Baeck et al. | |
| 5,691,297 A | 11/1997 | Nassano et al. | |
| 5,856,164 A | 1/1999 | Outtrup et al. | |
| 5,879,584 A | 3/1999 | Bianchetti et al. | |
| 6,020,303 A | 2/2000 | Cripe et al. | |
| 6,060,443 A | 5/2000 | Cripe et al. | |
| 6,187,576 B1 | 2/2001 | Svendsen et al. | |
| 6,225,464 B1 | 5/2001 | Hiler, II et al. | |
| 6,291,412 B1 | 9/2001 | Kvita et al. | |
| 6,306,812 B1 | 10/2001 | Perkins et al. | |
| 6,312,936 B1 | 11/2001 | Poulose et al. | |
| 6,326,348 B1 | 12/2001 | Vinson et al. | |
| 6,818,804 B1 | 11/2004 | Gonsalves et al. | |
| 6,939,702 B1 | 9/2005 | Vind et al. | |
| 2003/0087790 A1 | 5/2003 | Puelle Andrade et al. | |
| 2003/0087791 A1 | 5/2003 | Bonelli et al. | |
| 2004/0048764 A1 | 3/2004 | Kim et al. | |
| 2005/0003983 A1 | 1/2005 | Kim et al. | |
| 2005/0112749 A1 | 5/2005 | Outtrup et al. | |
| 2005/0227891 A1 | 10/2005 | Dreyer et al. | |

FOREIGN PATENT DOCUMENTS

| | | |
|---|---|---|
| WO | WO 96/39528 A2 | 12/1996 |
| WO | WO 98/17767 A1 | 4/1998 |
| WO | WO 98/26078 A1 | 6/1998 |
| WO | WO 99/51714 A2 | 10/1999 |
| WO | WO 00/32601 A2 | 6/2000 |
| WO | WO 01/05874 A1 | 1/2001 |
| WO | WO 01/47956 A2 | 7/2001 |
| WO | WO 2005/042532 A1 | 5/2005 |

OTHER PUBLICATIONS

Chica et al. Curr Opin Biotechnol. Aug. 2005;16(4):378-84.*
Sen et al. Appl Biochem Biotechnol. Dec. 2007;143(3):212-23*
Mitidieri et al. Bioresour Technol. Jul. 2006;97(10):1217-24. Epub Aug. 19, 2005.*
Stoner, Michael R et al., Ca2+- Surfactant Interactions Affect Enzyme Stability in Detergent Solutions, Biotechnology Progress, Nov. 2005, vol. 21, No. 6, pp. 1716-1723.
Igarashi, Kazuaki et al., Improved Thermostability of a Bacillus Alpha-amylase by Deletion of an Arginine-Glycine Residue Is Caused by Enhanced Calcium Binding, Biochemical And Biophysical Research Communications, Jul. 20, 1998, vol. 248, No. 2, pp. 372-377.
International Search Report, Mailed May 23, 2008, 7 pages, for International Application No. PCT/IB 2007/052309.
Fleet, Bernard et al., Investigation of the Factors Affecting the Response Time of a Calcium Selective Liquid Membrane Electrode, Analytical Chemistry, Jan. 1974, vol. 46, No. 1, pp. 12-15.
Butler, J. E., The Immunochemistry of sandwich ELISA's: Principles and Applications for the Quantitative Determination of Immunoglobulins, ELISA and Other Solid Phase Immunoassays, 1988, pp. 155-180, John Wiley and Sons, NY.
Miller, Larry S. et al., A Robotic Immunoassay System for Detergent Enzymes, Laboratory Information Management, 1994, vol. 26, pp. 79-87.

* cited by examiner

*Primary Examiner*—Christian L Fronda
(74) *Attorney, Agent, or Firm*—James F. McBride; Kim William Zerhy; Steven W. Miller

(57) ABSTRACT

This invention relates to compositions comprising certain amylase variants and processes for making and using such compositions including the use of such compositions to clean and/or treat a situs.

12 Claims, No Drawings

CLEANING AND/OR TREATMENT COMPOSITIONS

CROSS-REFERENCES TO RELATED APPLICATIONS

This application claims priority under 35 U.S.C. §119(e) to U.S. Provisional Application Ser. No. 60/814,442 filed Jun. 16, 2006.

FIELD OF INVENTION

Compositions comprising enzymes and processes for making and using such compositions.

BACKGROUND OF THE INVENTION

The appearance of enzymes suitable for cleaning and/or treatment applications gave the formulator a new approach to clean and/or treat hard surfaces and fabrics. Unfortunately, even when enzymes are employed, performance issues remain. For example, in certain matrices and/or use conditions, enzymes do not deposit as efficiently as required to provide the desired performance. Thus, the use of this technology continues to be limited.

Surprisingly, when cleaning compositions that comprise certain α-amylases are formulated in accordance with the teachings of the present invention, such compositions can provide improved cleaning.

SUMMARY OF THE INVENTION

This invention relates to compositions comprising certain α-amylase enzymes and processes for making and using such products.

DETAILED DESCRIPTION OF THE INVENTION

Definitions

As used herein, the term "cleaning composition" includes, unless otherwise indicated, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the phrase "is independently selected from the group consisting of . . . " means that moieties or elements that are selected from the referenced Markush group can be the same, can be different or any mixture of elements.

As used herein, articles, for example, "a" and "an" when used in a claim, are understood to mean one or more of what is claimed or described.

As used herein, the terms "include", "includes" and "including" are meant to be non-limiting.

The test methods disclosed in the Test Methods Section of the present application must be used to determine the respective values of the parameters of Applicants' inventions.

Unless otherwise noted, all component or composition levels are in reference to the active level of that component or composition, and are exclusive of impurities, for example, residual solvents or by-products, which may be present in commercially available sources.

Unless otherwise noted, the enzymes of the present invention are expressed in terms of active protein level and are exclusive of impurities, for example, residual solvents or by-products, which may be present in commercially available sources.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Compositions

In one aspect, a composition comprising an amylase and:
a.) a sufficient amount of calcium to provide a wash liquor comprising said composition with a free calcium concentration as determined by Test Method 1 of from about 0.1 ppm to about 500 ppm, from about 0.2 ppm to about 200 ppm, from about 1 ppm to about 150 ppm, or from about 2 ppm to about 100 ppm, or even from about 3 ppm to about 50 ppm;
b.) based on total product weight, less than 15%, less than 10%, less than 8% or even from about 0.01% to about 7% builder; and/or
c.) having an enzyme deposition index as defined in Test Method 2 of at least 2.5, at least 2.6, or even from about 2.7 to about 50 is disclosed.

Such composition may comprise, based on total composition weight, from about 0.0001% to about 2%, from about 0.0005% to about 1%, from about 0.001% to about 0.5% or even from about 0.002% to about 0.25% of said enzyme. Such compositions may be cleaning and/or treatment compositions. Thus it is understood that they may be solids or fluids.

In one aspect, said amylase includes α-amylases derived from *Bacillus lichenformis* having SEQ ID NO: 5 or 6, or an enzyme that is at least 65%, 70%, 75%, 80%, 85%, 90%, 95%, or even 99% identical to said SEQ ID NO: 5 or 6. Such α-amylases having at least one of the following mutations at positions corresponding to the positions corresponding to SEQ ID NO: 5 or 6: 15, 23, 133, 188, 209, 475 or combinations of said positions.

In another aspect, said amylase enzymes include α-amylases derived from *Bacillus lichenformis* having SEQ ID NO:5 (SEQ ID NO: 5 herein being equivalent to SEQ ID NO: 34 in U.S. Pat. No. 5,958,739) or an enzyme having at least 65%, 70%, 75%, 80%, 85%, 90%, 95%, or even 99% identity to said SEQ ID NO: 5. Such α-amylases having one or more of the following mutations: M15T, H133Y, N188S or T, A209V or G475R.

In another aspect, said amylase enzymes include α-amylases derived from *Bacillus lichenformis* having SEQ ID NO: 6 (SEQ ID NO: 6 herein being equivalent to SEQ ID NO: 2 in U.S. Pat. No. 6,436,888 B1) or an enzyme having at least 65%, 70%, 75%, 80%, 85%, 90%, 95%, or even 99% identity to said SEQ ID NO: 6. Such α-amylases having one or more of the following mutations: M15T, H133Y, N188S or T, A209V or G475R; and optionally R23K.

In another aspect, said amylase enzymes include an amylase selected from the group consisting of:
a.) an amylase having SEQ ID NO: 5, said amylase having one of the following groups of mutations:
  (i) M15T+H133Y+N188S+A209V;
  (ii) M15T+H133Y+N188T+A209V;
  (iii) H133Y+N188S+G475R; or
  (iv) H133Y+N188S;
b.) an amylase having SEQ ID NO: 6, said amylase having one of the following groups of mutations:
  (i) M15T+R23K+H133Y+N188S+A209V;
  (ii) M15T+R23K+H133Y+N188T+A209V;
  (iii) R23K+H133Y+N188S+G475R;
  (iv) R23K+H133Y+N188S;
  (v) M15T+H133Y+N188S+A209V
  (vi) M15T+H133Y+N188T+A209V;
  (vii) H133Y+N188S+G475R; or
  (viii) H133Y+N188S and combinations thereof.

In one aspect, a composition comprising an amylase belonging to EC 3.2.1.1 such as an enzyme having SEQ ID NO: 1 and:
a.) a sufficient amount of calcium to provide a wash liquor comprising said composition with a free calcium concentration as determined by Test Method 1 of from about 0.1 ppm to about 500 ppm, from about 0.2 ppm to about 200 ppm, from about 1 ppm to about 150 ppm, or from about 2 ppm to about 100 ppm, or even from about 3 ppm to about 50 ppm;
b.) based on total product weight, less than 15%, less than 10%, less than 8% or even from about 0.01% to about 7% builder; and/or
c.) having an enzyme deposition index as defined in Test Method 2 of at least 2.5, at least 2.6, or even from about 2.7 to about 50 is disclosed.

Such composition may comprise, based on total composition weight, from about 0.0001% to about 2%, from about 0.0005% to about 1%, from about 0.001% to about 0.5% or even from about 0.002% to about 0.25% of said enzyme. Such compositions may be cleaning and/or treatment compositions. Thus it is understood that they may be solids or fluids.

Any of the aspects of said compositions described in the present specification may comprise a material selected from the group consisting of surfactants, builders, chelating agents, dye transfer inhibiting agents, dispersants, additional enzymes, and enzyme stabilizers, catalytic materials, bleaching agents, polymeric dispersing agents, clay soil removal/anti-redeposition agents, brighteners, suds suppressors, dyes, perfumes, structure elasticizing agents, fabric softeners, carriers, hydrotropes, processing aids, solvents, pigments, hueing agents, structurants, and mixtures thereof.

Any of the aspects of said compositions described in the present specification may comprise an additional enzyme selected from the group consisting of hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, glucanases, arabinosidases, hyaluronidase, chondroitinase, laccase, amylases, or mixtures thereof.

In one aspect, such additional enzyme may be selected from the group consisting of: lipases, including "first cycle lipases" described in U.S. Pat. No. 6,939,702 B1 (SEQ ID NO: 2 in the present specification being equivalent to SEQ ID NO: 1 in U.S. Pat. No. 6,939,702 B1), a variant of SEQ ID NO: 2, a variant of SEQ ID NO: 2 having at least 90% identity to SEQ ID NO: 2 comprising a substitution of an electrically neutral or negatively charged amino acid with R or K at any of positions 3, 224, 229, 231 and 233, or even a variant comprising T231R and N233R mutations, such variant being sold under the tradename Lipex®; alpha-amylases, including a variant of SEQ ID NO: 3 (SEQ ID NO: 3 corresponding to SEQ ID NO: 2 in U.S. Pat. No. 5,856,164), a variant of SEQ ID NO: 3 having at least 90% identity to SEQ ID NO:3 (such variant disclosed in U.S. No. 6,187,576) comprising two deletions at positions 183 and 184 and sold under the tradename Natalase®; serine proteases, including neutral or alkaline microbial serine proteases, such as subtilisins (EC 3.4.21.62), including those derived from *Bacillus lentus, B. alkalophilus, B. subtilis, B. amyloiquefaciens* described in U.S. Pat. Nos. 6,312,936 B1, 5,679,630, 4,760,025; microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence of SEQ ID NO: 4 (SEQ ID NO: 4 herein being equivalent to SEQ ID NO: 2 in US 2005/0112749 A1)—such an enzyme being commercially available under the tradename Celluclean™ by Novozymes A/S, and mixtures thereof.

Any of the aspects of the compositions described in the present specification may comprise a surfactant, including a surfactant selected from the group of anionic surfactants including anionic surfactants selected from the group consisting of linear alkylbenzene-sulfonate (LAS), alcohol ethoxysulfate (AES), mid-branched alkyl sulfates (HSAS) and mixtures thereof; non-ionic surfactants including alcohol ethoxylates, for example alcohol ethoxylates having a chain length of from 1 to 14 carbons, or 12 to 14 carbons; amine oxides and mixtures thereof.

Any of the aspects of the compositions described in the present specification may comprise a polymer, including polymers selected from the group consisting of polyacrylates, maleic/acrylic acid copolymers, cellulose-derived polymers, including carboxymethylcellulose and methyl hydroxyethylcellulose, polyethyleneimine polymers and mixtures thereof.

Any of the aspects of said compositions described in the present specification may comprise a builder selected from the group consisting of citric acid, $C_{12}$-$C_{18}$ fatty acid, aluminosilicates, including zeolites A, X and/or Y, sodium tripolyphosphate and mixtures thereof.

Any of the aspects of the compositions described in the present specification may comprise a material selected from the group consisting of a photobleach, a fabric hueing agent and mixtures thereof.

Any of the aspects of the compositions described in the present specification may comprise a photobleach being selected from the group consisting of xanthene dyes and mixtures thereof; sulfonated zinc phthalocyanine, sulfonated aluminium phthalocyanine, Eosin Y, Phoxine B, Rose Bengal, C.I. Food Red 14 and mixtures thereof; water soluble phthalocyanine; and/or a fabric hueing agent selected from the group consisting of dyes, including small molecule dyes such as small molecule dyes selected from the group consisting of Colour Index (Society of Dyers and Colourists, Bradford, UK) numbers Direct Violet 9, Direct Violet 35, Direct Violet 48, Direct Violet 51, Direct Violet 66, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Violet 49, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159 and mixtures thereof, polymeric dyes and mixtures thereof, dye-clay conjugates comprising at least one cationic/basic dye and a smectite clay and mixtures thereof.

Any of the aspects of the compositions described in the present specification may comprise, based on total product weight, from about 0% to about 3%, from about 0.0001% to about 0.5%, or even from about 0.0005% to about 0.3% photobleach and/or from about 0.00003% to about 0.3%, from about 0.00008% to about 0.05%, or even from about 0.0001% to about 0.04% hueing agent.

Enzymes suitable for use in the present compositions can be obtained from Genencor International, Palo Alto, Calif., U.S.A; Novozymes A/S, Bagsvaerd, Denmark; Amersham Pharmacia Biotech., Piscataway, N.J., U.S.A; Sigma-Aldrich Company Ltd, Dorset, UK.

An enzyme having SEQ ID NO: 1 is sold under the tradename Optisize® HT Plus by Genencor International, Palo Alto, Calif., U.S.A. An enzyme having at least 90% identity to SEQ ID NO: 2 is sold under the tradename Lipex® by Novozymes A/S, Bagsvaerd, Denmark. An enzyme having at least 90% identity with SEQ ID NO: 3 is sold under the tradename Natalase® by Novozymes A/S, Bagsvaerd, Denmark. An enzyme having at least 90% identity to SEQ ID NO: 4 is sold under the tradename Celluclean™ by Novozymes A/S, Bagsvaerd, Denmark. An enzyme having SEQ ID NO: 5 is sold under the tradename of Purastar® by Genencor International, Palo Alto, Calif., U.S.A. An enzyme having SEQ ID NO: 6 is sold under the tradename of Termamyl® by Novozymes A/S, Bagsvaerd, Denmark.

Surfactants suitable for use in the present compositions can be obtained from Stepan, Northfield, Ill., USA; Huntsman, Salt Lake City, Utah, USA; Procter & Gamble Chemicals, Cincinnati, Ohio, USA.

Builders suitable for use in the present compositions can be obtained from Rhodia, Paris, France; Industrial Zeolite (UK) Ltd, Grays, Essex, UK; Koma, Nestemica, Czech Republic.

Polymers suitable for use in the present compositions can be obtained from BASF, Ludwigshafen, Germany, CP Kelco, Amhem, Netherlands.

Photobleaches suitable for use in the present compositions can be obtained from Aldrich, Milwaukee, Wis., USA; Frontier Scientific, Logan, Utah, USA; Ciba Specialty Chemicals, Basel, Switzerland; BASF, Ludwigshafen, Germany; Lamberti S.p.A, Gallarate, Italy; Dayglo Color Corporation, Mumbai, India; Organic Dyestuffs Corp., East Providence, R.I., USA.

Hueing agents suitable for use in the present compositions can be obtained from Aldrich, Milwaukee, Wis., USA; Ciba Specialty Chemicals, Basel, Switzerland; BASF, Ludwigshafen, Germany; Dayglo Color Corporation, Mumbai, India; Organic Dyestuffs Corp., East Providence, R.I., USA; Dystar, Frankfurt, Germany; Lanxess, Leverkusen, Germany; Megazyme, Wicklow, Ireland; Clariant, Muttenz, Switzerland.

Adjunct Materials

While not essential for the purposes of the present invention, the non-limiting list of adjuncts illustrated hereinafter are suitable for use in the instant compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. The precise nature of these additional components, and levels of incorporation thereof, will depend on the physical form of the composition and the nature of the cleaning operation for which it is to be used. Suitable adjunct materials include, but are not limited to, additional surfactants, additional builders, additional polymers, additional hueing agents, additional photobleaches, chelating agents, dye transfer inhibiting agents, dispersants, additional enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents, additional hueing agents, structurants and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' compositions. Thus, certain embodiments of Applicants' compositions do not contain one or more of the following adjuncts materials: additional surfactants, additional builders, additional polymers, additional photobleaches, chelating agents, dye transfer inhibiting agents, dispersants, additional enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents, additional hueing agents, structurants and/or pigments. However, when one or more adjuncts are present, such one or more adjuncts may be present as detailed below:

Bleaching Agents—The cleaning compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) photobleaches (2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone®, and mixtures thereof. Suitable percarboxylic acids include hydrophobic and hydrophilic peracids having the formula R—(C=O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counter ion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof.

When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Surfactants—The cleaning compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. When present, surfactant is typically present at a level of from about 0.1% to about 60%, from about 1% to about 50% or even from about 5% to about 40% by weight of the subject composition.

Builders—The cleaning compositions of the present invention may comprise one or more detergent builders or builder systems. Builders include, but are not limited to, the alkali metal, ammonium and alkanolammonium salts of polyphosphates, alkali metal silicates, alkaline earth and alkali metal carbonates, aluminosilicate builders and polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

Chelating Agents—The cleaning compositions herein may contain a chelating agent. Suitable chelating agents include copper, iron and/or manganese chelating agents and mixtures thereof. When a chelating agent is used, the subject composition may comprise from about 0.005% to about 15% or even from about 3.0% to about 10% chelating agent by weight of the subject composition.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Brighteners—The cleaning compositions of the present invention can also contain additional components that may tint articles being cleaned, such as fluorescent brighteners. Suitable fluorescent brightener levels include lower levels of from about 0.01, from about 0.05, from about 0.1 or even from about 0.2 wt % to upper levels of 0.5 or even 0.75 wt %.

Dispersants—The compositions of the present invention can also contain dispersants. Suitable water-soluble organic materials include the homo- or co-polymeric acids or their salts, in which the polycarboxylic acid comprises at least two carboxyl, radicals separated from each other by not more than two carbon atoms.

Enzymes—The cleaning compositions can comprise one or more enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, glucanases, arabinosidases, hyaluronidase, chondroitinase, laccase, amylases, or mixtures thereof. A typical combination is an enzyme cocktail that may comprise, for example, a protease and lipase in conjunction with amylase. When present in a cleaning composition, the aforementioned additional enzymes may be present at levels from about 0.00001% to about 2%, from about 0.0001% to about 1% or even from about 0.001% to about 0.5% enzyme protein by weight of the composition.

Enzyme Stabilizers—Enzymes for use in detergents can be stabilized by various techniques. The enzymes employed herein can be stabilized by the presence of water-soluble sources of calcium and/or magnesium ions in the finished compositions that provide such ions to the enzymes. In case of aqueous compositions comprising protease, a reversible protease inhibitor, such as a boron compound, can be added to further improve stability.

Catalytic Metal Complexes—Applicants' cleaning compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936; 5,595,967. Such cobalt catalysts are readily prepared by known procedures, such as taught for example in U.S. Pat. Nos. 5,597,936, and 5,595,967.

Compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

Solvents—Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

Processes of Making Compositions

The compositions of the present invention can be formulated into any suitable form and prepared by any process chosen by the formulator, non-limiting examples of which are described in Applicants' examples and in U.S. Pat. No. 4,990,280; U.S. 20030087791A1; U.S. 20030087790A1; U.S. 20050003983A1; U.S. 20040048764A1; U.S. Pat. Nos. 4,762,636; 6,291,412; U.S. 20050227891A1; EP 1070115A2; U.S. Pat. Nos. 5,879,584; 5,691,297; 5,574,005; 5,569,645; 5,565,422; 5,516,448; 5,489,392; 5,486,303.

Method of Use

The present invention includes a method for cleaning and/or treating a situs inter alia a surface or fabric. Such method includes the steps of optionally washing and/or rinsing said surface or fabric, contacting said surface or fabric with a composition of the present invention in neat or diluted form such as in a wash liquor and then optionally washing and/or rinsing said surface or fabric. For purposes of the present invention, washing includes but is not limited to, scrubbing, and mechanical agitation. As will be appreciated by one skilled in the art, the cleaning compositions of the present invention are ideally suited for use in laundry applications. Accordingly, the present invention includes a method for laundering a fabric. The method may comprise the steps of contacting a fabric to be laundered with a said cleaning laundry solution comprising at least one embodiment of Applicants' cleaning composition, cleaning additive or mixture thereof. The fabric may comprise most any fabric capable of being laundered in normal consumer use conditions. The solution may have in one aspect a pH of from about 7.5 to about 10.5 or even a pH of from about 8 to about 10.5. The compositions may be employed at concentrations of from about 500 ppm to about 15,000 ppm in solution. The water temperatures typically range from about 5° C. to about 90° C. The water to fabric ratio is typically from about 1:1 to about 30:1.

Test Methods

Test Method 1—Procedure for Determining the Concentration of Free CALCIUM ($Ca^{++}$)

Basis of Method

Free calcium is assayed by using an ion specific electrode that is specific for calcium. This measurement technique is well known and is exemplified in many literature references, such as Analytical Chemistry, Vol 46, No 1, 1974, p. 12-15, and manuals exemplifying the use of such electrodes are broadly known and available (e.g. from Metrohm of Buckinghamshire, UK and from HACH LANGE LTD, Manchester, UK). The description below shows how such a technique may be applied to measurements of free calcium for detergents.

Calibration:

Before use, the electrodes must be calibrated. This may be done by measuring a series of known standard solutions, made by serial dilution of the 1000 ppm Calcium standard solution. For a full calibration, prepare 100 ml of solutions containing 1000, 100, 10, 1, and 0.1 ppm $Ca^{2+}$.

Add 2 ml of Ionic Strength Adjustment Buffer (ISAB) solution to each standard and mix. Prepare a calibration graph.

Sample Preparation a. To 6 separate 1 L volumetric flasks add, 0, 20, 30, 40, 50, 100 and 200 ml of 1000 ppm calcium standard solution and add deionised water to make the volume to 1 liter to make solutions containing 0, 20, 30, 40, 50, 100 & 200 ppm of calcium. Transfer each 1 liter calcium solution to a 1 liter tergotometer pot and stir for 10 mins on a standard tergotometer.

b. To 50 ml of each solution from Step a. above, add 1 ml of ISAB buffer and measure calcium. This serves to check that the initial solution contains the level of calcium expected.

c. To each tergotometer pot from Step a. above add sufficient detergent to give a detergent solution having the same concentration as would be realized by adding the detergent manufacturer's recommended dose of detergent to the standard volume within a washing machine or median hand-wash practices. (For example formulations 1-6, typical detergent concentration would be 1.5-3 g/liter; for example formulations 7-12, typical detergent concentration would be 8-9 g/liter; for example formulations 13-16, typical detergent concentration would be 1.5 g/liter; and for examples 17 & 18, typical detergent concentrations would be 8-9 g/liter). Stir for 10 mins.

d. To 50 ml of each solution from Step c., add 1 ml of ISAB buffer, immerse the electrode and take the calcium reading, once equilibrated (typically takes several seconds). This is the free calcium reading for the detergent composition.

Apparatus Used:

Ion-Selective Calcium Electrode: Ion-selective calcium electrodes are broadly available. The one used for this test is sourced from VWR International Ltd., Leicestershire, UK and comprises the following parts: Ion-Selective Electrode for calcium ion (such as ELIT 8041 PVC membrane); Reference electrode: single junction silver chloride (such as ELIT 001); Dual electrode head (such as ELIT 201); ELIT Computer Interface/Ion Analyser attached to a Dell PC.

Standard solutions: The 1000 ppm calcium chloride solution can be made by dissolving calcium chloride (sourced from Sigma Aldrich of Milwaukee, US) in deionized water, and the buffer solution (ISAB) comprising 4 Molar KCl can be sourced from VWR International Ltd., Leicestershire, UK.

Standard Tergotometer: (e.g. models available from Copley Scientific, Nottingham, UK such as that sold under catalogue number Dissolution Tester DIS 8000).

Test Method 2—Procedure for Determining Enzyme Deposition Index

Basis of Method:

This method compares the residual enzyme concentration of various amylases detectable by standard Double Antibody Sandwich ELISA (DAS-ELISA) methods, well known to those skilled in the art, by reaction with the appropriate antibodies (DAS-ELISA technique is exemplified in various patents, e.g. U.S. Pat. Nos. 5,188,937 & 6,818,804, and in various literature articles, e.g. L. S. Miller, "A robotic immunoassay system for detergent enzymes." Laboratory Information Management, 1994, Vol 26, pgs 79-87; Butler, J. E. "The immunochemistry of sandwich ELISA's: principles and applications for the quantitative determination of immunoglobulins." In "ELISA and Other Solid Phase Immunoassays. Theoretical and Practical Aspects" Eds Kemeny, D. M. and Challacombe, S. J. John Wiley and Sons, NY. 1988, pgs. 155-180 and references incorporated therein.) Standard calibration methods are used.

The enzyme deposition index (EDI) is the ratio of the (mass of test alpha-amylase protein extracted/g fabric) and the (mass of Termamyl® protein extracted/g fabric). Thus, the equation for cotton fabric is Equation 1. This method may be used, for example, to determine the suitability of an enzyme for use as a detergent ingredient and/or predict the performance of an enzyme in, for example, a detergent application.

$$EDI = (\text{Mass of test alpha-amylase protein extracted per g cotton})/(\text{Mass of Termamyl® extracted per g cotton}) \quad \text{Equation 1}$$

Sample Preparation

1. To separate tergotometer pots add 980 ml of water containing 145±10 ppm calcium and 2.0 g of sodium carbonate (sourced from Sigma Aldrich of Milwaukee, USA). Stir for 10 minutes to dissolve. Allow to equilibrate to 40° C.
2. Add 0.69 g of LAS (Linear alkylbenzenesulfonate having an average aliphatic carbon chain length $C_{11}$-$C_{12}$) and 0.38 g of AE3S ($C_{12-15}$ alkyl ethoxy (3) sulfate), both supplied by Stepan, Northfield, Ill., USA. Stir to dissolve.
3. Add liquid samples of the various enzymes to be studied to the different tergotometer pots to ensure 0.2 mg of amylase are present in each pot. One pot should contain 0.2 mg Termamyl® (available from Novozymes of Denmark) to act as the reference versus which the other enzymes are to be indexed.
4. Adjust the water volume in each pot to 1 liter, if needed, using water containing 145±10 ppm calcium. The resultant solution should contain 690 ppm of LAS, 380 ppm AE3S, 2000 ppm of sodium carbonate and 0.2 ppm of the enzyme.
5. To each tergotometer pot, add three standard cotton swatches (sourced ex. Center for Test Materials (CFT) B.V. of Holland) with fabric code CN03, each weighing 3.5±0.3 g. The total weight of cotton should be 10.5±0.5 g per tergotometer pot.
6. Start the tergotometer run (conditions are 40±2° C., 150 rpm and run time is 20 minutes).
7. After 20 minutes the fabrics are removed, hand squeezed until not excess liquid is visible and then rinsed for 5 minutes in a tergotometer in 1 liter of water containing 145±10 ppm calcium (conditions are 150 rpm agitation, with a water temperature of 25±2° C.).
8. The swatches are removed and hand squeezed to remove excess liquor and then allowed to air dry at room temperature for 3-5 hours.
9. An extraction buffer is prepared comprising of:
    a. 0.93 g/L 2-Amino-2-(hydroxymethyl)-1,3-propanediol (otherwise known as Trizma base);
    b. 4.96 g/L Sodium Thiosulphate pentahydrate;
    c. 0.147 g/L Calcium Chloride dehydrate;
    d. 29.22 g/L sodium Chloride;
    e. 1.0 g Sodium Azide; and
    f. 1.0 g/L Polyethylene glycol sorbitan monolaurate (otherwise known as Tween 20 with CAS# 9005-64-5)

The pH of the buffer is adjusted to pH=8 using 0.1 N hydrochloric acid prior to use.

All reagents are available from Sigma Aldrich Company Ltd. Dorset, UK.

10. Each swatch of known weight is placed in a separate 50 ml extraction tube and 25 ml of extraction buffer is added. The tube is hand shaken vigorously for 1 minute (+/−10 s) then left to stand for 15 minutes (+/−1 minute) then shaken vigorously again for 1 minute (+/−10 s). The tube is allowed to stand for a further 15 minutes (+/−1 minute) before given a final vigorous shaking for 1 minute (+/−10 s).
11. The resultant solution is assayed via standard ELISA methods using a Rosys Plato 7381 analyzer (Supplier Rosys Anthos GmbH Feldbachstr CH-8634 Hombrechtikon Switzerland or equivalent ELISA equipment such as those supplied by Dynex Technologies of Virginia, USA or Biotech of Vermont, USA).
12. From this assay by comparing to the standard calibration curve, the mass of amylase protein detected can be determined and the mass of enzyme extracted/g of fabric can be calculated.
13. The whole process (Steps 1-12) is repeated 3 more times to generate further sets of data.
14. The enzyme deposition index is then calculated by taking the average of 12 readings expressed in ng amylase protein/g fabric (these twelve readings come from the three pieces of cloth per pot from each of the four runs) for each enzyme and indexing such value to that observed for Termamyl® protein as shown in Equation 1.

Equipment Used

Standard Tergotometer (e.g. models available from Copley Scientific, Nottingham, UK such as that sold under catalogue number Dissolution Tester DIS 8000).

EXAMPLES

Unless otherwise indicated, materials can be obtained from Aldrich, P.O. Box 2060, Milwaukee, Wis. 53201, USA.

Examples 1-6

Granular laundry detergent compositions designed for hand washing or top-loading washing machines.

|  | 1 (wt %) | 2 (wt %) | 3 (wt %) | 4 (wt %) | 5 (wt %) | 6 (wt %) |
| --- | --- | --- | --- | --- | --- | --- |
| Linear alkylbenzenesulfonate | 20 | 22 | 20 | 15 | 20 | 20 |
| $C_{12-14}$ Dimethylhydroxyethyl ammonium chloride | 0.7 | 0.2 | 1 | 0.6 | 0.0 | 0 |
| AE3S | 0.9 | 1 | 0.9 | 0.0 | 0.5 | 0.9 |
| AE7 | 0.0 | 0.0 | 0.0 | 1 | 0.0 | 3 |
| Sodium tripolyphosphate | 5 | 0.0 | 4 | 9 | 2 | 0.0 |
| Zeolite A | 0.0 | 1 | 0.0 | 1 | 4 | 1 |
| 1.6R Silicate ($SiO_2$:$Na_2O$ at ratio 1.6:1) | 7 | 5 | 2 | 3 | 3 | 5 |
| Sodium Carbonate | 25 | 20 | 25 | 17 | 18 | 19 |
| Polyacrylate MW 4500 | 1 | 0.6 | 1 | 1 | 1.5 | 1 |
| Carboxy Methyl Cellulose | 1 | 0.3 | 1 | 1 | 1 | 1 |
| Amylase* (20 mg active/g) | 0.1 | 0.2 | 0.1 | 0.2 | 0.1 | 0.1 |
| Savinase ® (32.89 mg active/g) | 0.1 | 0.1 | 0.1 | 0.1 | 0.1 | 0.1 |
| Natalase ® (8.65 mg active/g) | 0.1 | 0.0 | 0.1 | 0.0 | 0.1 | 0.1 |
| Lipex ® (18 mg active/g) | 0.03 | 0.07 | 0.3 | 0.1 | 0.07 | 0.4 |
| Fluorescent Brightener 1 | 0.06 | 0.0 | 0.06 | 0.18 | 0.06 | 0.06 |
| Fluorescent Brightener 2 | 0.1 | 0.06 | 0.1 | 0.0 | 0.1 | 0.1 |
| DTPA | 0.6 | 0.8 | 0.6 | 0.25 | 0.6 | 0.6 |
| $MgSO_4$ | 1 | 1 | 1 | 0.5 | 1 | 1 |
| Sodium Percarbonate | 0.0 | 5.2 | 0.1 | 0.0 | 0.0 | 0.0 |
| Sodium Perborate Monohydrate | 4.4 | 0.0 | 3.85 | 2.09 | 0.78 | 3.63 |
| NOBS | 1.9 | 0.0 | 1.66 | 0.0 | 0.33 | 0.75 |
| TAED | 0.58 | 1.2 | 0.51 | 0.0 | 0.015 | 0.28 |
| Sulphonated zinc phthalocyanine | 0.0030 | 0.0 | 0.0012 | 0.0030 | 0.0021 | 0.0 |
| S-ACMC | 0.1 | 0.0 | 0.0 | 0.0 | 0.06 | 0.0 |
| Direct Violet 9 | 0.0 | 0.0 | 0.0003 | 0.0005 | 0.0003 | 0.0 |
| Acid Blue 29 | 0.0 | 0.0 | 0.0 | 0.0 | 0.0 | 0.0003 |
| Sulfate/Moisture* | | | | | | |

*Balance to 100% for Examples 1-6

Examples 7-12

Granular laundry detergent compositions designed for front-loading automatic washing machines.

|  | 7 (wt %) | 8 (wt %) | 9 (wt %) | 10 (wt %) | 11 (wt %) | 12 (wt %) |
| --- | --- | --- | --- | --- | --- | --- |
| Linear alkylbenzenesulfonate | 8 | 7.1 | 7 | 6.5 | 7.5 | 7.5 |
| AE3S | 0 | 4.8 | 0 | 5.2 | 4 | 4 |
| Alkylsulfate | 1 | 0 | 1 | 0 | 0 | 0 |
| AE7 | 2.2 | 0 | 3.2 | 0 | 0 | 0 |
| $C_{10-12}$ Dimethyl hydroxyethylammonium chloride | 0.75 | 0.94 | 0.98 | 0.98 | 0 | 0 |
| Crystalline layered silicate ($\delta$-$Na_2Si_2O_5$) | 4.1 | 0 | 4.8 | 0 | 0 | 0 |
| Zeolite A | 5 | 0 | 5 | 0 | 2 | 2 |
| Citric Acid | 3 | 5 | 3 | 4 | 2.5 | 3 |
| Sodium Carbonate | 15 | 20 | 14 | 20 | 23 | 23 |
| Silicate 2R ($SiO_2$:$Na_2O$ at ratio 2:1) | 0.08 | 0 | 0.11 | 0 | 0 | 0 |
| Soil release agent | 0.75 | 0.72 | 0.71 | 0.72 | 0 | 0 |
| Acrylic Acid/Maleic Acid Copolymer | 1.1 | 3.7 | 1.0 | 3.7 | 2.6 | 3.8 |
| Carboxymethylcellulose | 0.15 | 1.4 | 0.2 | 1.4 | 1 | 0.5 |
| Protease (84 mg active/g) | 0.2 | 0.2 | 0.3 | 0.15 | 0.12 | 0.13 |
| Amylase* (20 mg active/g) | 0.2 | 0.15 | 0.2 | 0.3 | 0.15 | 0.15 |
| Lipex ® (18.00 mg active/g) | 0.05 | 0.15 | 0.1 | 0 | 0 | 0 |
| Natalase ® (8.65 mg active/g) | 0.1 | 0.2 | 0 | 0 | 0.15 | 0.15 |
| Celluclean ™ (15.6 mg active/g) | 0 | 0 | 0 | 0 | 0.1 | 0.1 |
| TAED | 3.6 | 4.0 | 3.6 | 4.0 | 2.2 | 1.4 |
| Percarbonate | 13 | 13.2 | 13 | 13.2 | 16 | 14 |
| Na salt of Ethylenediamine-N,N'-disuccinic acid, (S,S) isomer (EDDS) | 0.2 | 0.2 | 0.2 | 0.2 | 0.2 | 0.2 |
| Hydroxyethane di phosphonate (HEDP) | 0.2 | 0.2 | 0.2 | 0.2 | 0.2 | 0.2 |

-continued

|  | 7 (wt %) | 8 (wt %) | 9 (wt %) | 10 (wt %) | 11 (wt %) | 12 (wt %) |
|---|---|---|---|---|---|---|
| MgSO$_4$ | 0.42 | 0.42 | 0.42 | 0.42 | 0.4 | 0.4 |
| Perfume | 0.5 | 0.6 | 0.5 | 0.6 | 0.6 | 0.6 |
| Suds suppressor agglomerate | 0.05 | 0.1 | 0.05 | 0.1 | 0.06 | 0.05 |
| Soap | 0.45 | 0.45 | 0.45 | 0.45 | 0 | 0 |
| Sulphonated zinc phthalocyanine (active) | 0.0007 | 0.0012 | 0.0007 | 0 | 0 | 0 |
| S-ACMC | 0.01 | 0.01 | 0 | 0.01 | 0 | 0 |
| Direct Violet 9 (active) | 0 | 0 | 0.0001 | 0.0001 | 0 | 0 |
| Sulfate/Water & Miscellaneous* | | | | | | |

*Balance to 100% for Examples 7-12

Any of the above compositions is used to launder fabrics at a concentration of 7000 to 10000 ppm in water, 20-90° C., and a 5:1 water:cloth ratio. The typical pH is about 10.

Examples 13-18

Heavy Duty Liquid Laundry Detergent Compositions

Raw Materials and Notes For Composition Examples 1-18

Raw Materials and Notes For Composition Examples 1-18

Linear alkylbenzenesulfonate having an average aliphatic carbon chain length $C_{11}$-$C_{12}$ supplied by Stepan, Northfield, Ill., USA $C_{12-14}$ Dimethylhydroxyethyl ammonium chloride, supplied by Clariant GmbH, Sulzbach, Germany AE3S is $C_{12-15}$ alkyl ethoxy (3) sulfate supplied by Stepan, Northfield, Ill., USA

|  | 13 (wt %) | 14 (wt %) | 15 (wt %) | 16 (wt %) | 17 (wt %) | 18 (wt %) |
|---|---|---|---|---|---|---|
| AES $C_{12-15}$ alkyl ethoxy (1.8) sulfate | 11 | 10 | 4 | 6.32 | 0 | 0 |
| AE3S | 0 | 0 | 0 | 0 | 2.4 | 0 |
| Linear alkyl benzene sulfonate | 1.4 | 4 | 8 | 3.3 | 5 | 8 |
| HSAS | 3 | 5.1 | 3 | 0 | 0 | 0 |
| Sodium formate | 1.6 | 0.09 | 1.2 | 0.04 | 1.6 | 1.2 |
| Sodium hydroxide | 2.3 | 3.8 | 1.7 | 1.9 | 1.7 | 2.5 |
| Monoethanolamine | 1.4 | 1.49 | 1.0 | 0.7 | 0 | 0 |
| Diethylene glycol | 5.5 | 0.0 | 4.1 | 0.0 | 0 | 0 |
| Nonionic 23,9 | 0.4 | 0.6 | 0.3 | 0.3 | 0 | 0 |
| Nonionic 24,7 | 0 | 0 | 0 | 0 | 2.4 | 6 |
| Chelant | 0.15 | 0.15 | 0.11 | 0.07 | 0.5 | 0.11 |
| Citric Acid | 2.5 | 3.96 | 1.88 | 1.98 | 0.9 | 2.5 |
| $C_{12-14}$ dimethyl Amine Oxide | 0.3 | 0.73 | 0.23 | 0.37 | 0 | 0 |
| $C_{12-18}$ Fatty Acid | 0.8 | 1.9 | 0.6 | 0.99 | 3.5 | 2.5 |
| Borax | 1.43 | 1.5 | 1.1 | 0.75 | 1 | 1.07 |
| Ethanol | 1.54 | 1.77 | 1.15 | 0.89 | 0 | 3 |
| Ethoxylated (EO$_{15}$) tetraethylene pentaimine[1] | 0.3 | 0.33 | 0.23 | 0.17 | 0.0 | 0.0 |
| Ethoxylated hexamethylene diamine[2] | 0.8 | 0.81 | 0.6 | 0.4 | 1 | 1 |
| 1,2-Propanediol | 0.0 | 6.6 | 0.0 | 3.3 | 0.5 | 2 |
| Protease (40.6 mg active/g) | 0.8 | 0.6 | 0.7 | 0.9 | 0.7 | 0.6 |
| Mannaway ® (25 mg active/g) | 0.07 | 0.05 | 0.045 | 0.06 | 0.04 | 0.045 |
| Amylase* (15 mg active/g) | 0.3 | 0.2 | 0.3 | 0.1 | 0.2 | 0.4 |
| Natalase ® (29 mg active/g) | 0 | 0.2 | 0.1 | 0.15 | 0.07 | 0 |
| Lipex ® (18 mg active/g) | 0.4 | 0.2 | 0.3 | 0.1 | 0.2 | 0 |
| Liquitint ® Violet CT (active) | 0.006 | 0.002 | 0 | 0 | 0 | 0.002 |
| S-ACMC | — | — | 0.01 | 0.05 | 0.01 | 0.02 |
| Water, perfume, dyes & other components | Balance | Balance | Balance | Balance | Balance | Balance |

AE7 is $C_{12-15}$ alcohol ethoxylate, with an average degree of ethoxylation of 7, supplied by Huntsman, Salt Lake City, Utah, USA Sodium tripolyphosphate is supplied by Rhodia, Paris, France Zeolite A is supplied by Industrial Zeolite (UK) Ltd, Grays, Essex, UK 1.6R Silicate is supplied by Koma, Nestemica, Czech Republic Sodium Carbonate is supplied by Solvay, Houston, Tex., USA Polyacrylate MW 4500 is supplied by BASF, Ludwigshafen, Germany Carboxy Methyl Cellulose is Finnfix® BDA supplied by CP Kelco, Arnhem, Netherlands Suitable chelants are, for example, diethylenetetraamine pentaacetic acid (DTPA) supplied by Dow Chemical, Midland, Mich., USA or Hydroxyethane di phosphonate (HEDP) supplied by Solutia, St. Louis, Mo., USA Bagsvaerd, Denmark Protease (examples 7-12) described in U.S. Pat. No. 6,312,936 B1 supplied by Genencor International, Palo Alto, Calif., USA Protease (examples 13-18) described in U.S. Pat. No. 4,760,025 is supplied by Genencor International, Palo Alto, Calif., USA

* A suitable amylase is, for example, Optisize® HT Plus supplied by Genencor International, Palo Alto, Calif., USA, or any of the other amylases specifically described in the present specification.

Fluorescent Brightener 1 is Tinopal® AMS, Fluorescent Brightener 2 is Tinopal® CBS-X, Sulphonated zinc phthalocyanine and Direct Violet 9 is Pergasol® Violet BN-Z all supplied by Ciba Specialty Chemicals, Basel, Switzerland Sodium percarbonate supplied by Solvay, Houston, Tex., USA Sodium perborate is supplied by Degussa, Hanau, Germany NOBS is sodium nonanoyloxybenzenesulfonate, supplied by Eastman, Batesville, Ark., USA TAED is tetraacetylethylenediamine, supplied under the Peractive® brand name by Clariant GmbH, Sulzbach, Germany S-ACMC is carboxymethylcellulose conjugated with C.I. Reactive Blue 19, sold by Megazyme, Wicklow, Ireland under the product name AZO-CM-CELLULOSE, product code S-ACMC.

Soil release agent is Repel-o-tex® PF, supplied by Rhodia, Paris, France

Acrylic Acid/Maleic Acid Copolymer is molecular weight 70,000 and acrylate:maleate ratio 70:30, supplied by BASF, Ludwigshafen, Germany Na salt of Ethylenediamine-N,N'-disuccinic acid, (S,S) isomer (EDDS) is supplied by Octel, Ellesmere Port, UK Hydroxyethane di phosphonate (HEDP) is supplied by Dow Chemical, Midland, Mich., USA Suds suppressor agglomerate is supplied by Dow Corning, Midland, Mich., USA HSAS is mid-branched alkyl sulfate as disclosed in U.S. Pat. Nos. 6,020,303 and 6,060,443

$C_{12-14}$ dimethyl Amine Oxide is supplied by Procter & Gamble Chemicals, Cincinnati, Ohio, USA Liquitint® Violet CT is supplied by Milliken, Spartanburg, S.C., USA)

[1] as described in U.S. Pat. No. 4,597,898.

[2] available under the tradename LUTENSIT® from BASF and such as those described in WO 01/05874

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising an amylase selected from the group consisting of:
   a.) an amylase having SEQ. ID NO: 5, said amylase having one of the following groups of mutations:
      (i) M15T+H133Y+N188S+A209V;
      (ii) M15T+H133Y+N188T+A209V;
      (iii) H133Y+N188S+G475R; or
      (iv) H133Y+N188S;
   b.) an amylase having SEQ. ID NO: 6, said amylase having one of the following groups of mutations:
      (i) M15T+R23K+H133Y+N188S+A209V;
      (ii) M15T+R23K+H133Y+N188T+A209V;
      (iii) R23K+H133Y+N188S+G475R;
      (iv) R23K+H133Y+N188S;
      (v) M15T+H133Y+N188S+A209V;
      (vi) M15T+H133Y+N188T+A209V;
      (vii) H133Y+N188S+G475R; or
      (viii) H133Y+N188S
   c.) and combinations thereof
   and a sufficient amount of calcium to provide a wash liquor comprising said composition with a free calcium concentration of from about 0.1 ppm to about 500 ppm.

2. The composition of claim 1, said composition comprising a material selected from the group consisting of surfactants, builders, chelating agents, dye transfer inhibiting agents, dispersants, additional enzymes, and enzyme stabilizers, catalytic materials, bleaching agents, polymeric dispersing agents, clay soil removal/anti-redeposition agents, brighteners, suds suppressors, dyes, perfumes, structure elasticizing agents, fabric softeners, carriers, hydrotropes, processing aids, solvents, pigments, hueing agents, photobleaches, structurants, and mixtures thereof, and being a tablet, paste, gel, granular, liquid or rinse aid cleaning composition.

3. The composition of claim 2, said composition comprising an additional enzyme.

4. The composition of claim 3, wherein said additional enzyme is selected from the group consisting of hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, glucanases, arabinosidases, hyaluronidase, chondroitinase, laccase, amylases, or mixtures thereof.

5. The composition of claim 4, wherein said additional enzyme is selected from the group consisting of:
   a.) lipases
   b.) alpha-amylases;

c.) serine proteases;
d.) microbial-derived endoglucanases; and
e.) mixtures thereof.

6. The composition of claim 2, said composition comprising a surfactant selected from the group of:
  a.) anionic surfactants selected from the group consisting of linear alkylbenzene-sulfonate (LAS), alcohol ethoxysulfate (AES), mid-branched alkyl sulfates (HSAS) and mixtures thereof;
  b.) non ionic alcohol ethoxylates;
  c.) amine oxides; and
  d.) mixtures thereof.

7. The composition of claim 2, said composition comprising a polymer selected from the group consisting of
  a.) polyacrylates;
  b.) maleic/acrylic acid copolymers;
  c.) cellulose-derived polymers;
  d.) polyethyleneimine polymer; and
  e.) mixtures thereof.

8. The composition of claim 2, said composition comprising a builder selected from the group consisting of
  a.) citric acid;
  b.) $C_{12}$-$C_{18}$ fatty acid;
  c.) aluminosilicates;
  d.) sodium tripolyphosphate; and
  e.) mixtures thereof.

9. The composition of claim 8, said composition comprising, based on total product weight, less than 15% builder.

10. The composition of claim 2, said composition comprising a material selected from the group consisting of a photobleach, a fabric hueing agent and mixtures thereof, said photobleach being selected from the group consisting of
  a.) xanthene dyes;
  b.) sulfonated zinc phthalocyanine, sulfonated aluminium phthalocyanine, Eosin Y, Phoxine B, Rose Bengal, C.I. Food Red 14 and mixtures thereof;
  c.) water soluble phthalocyanine; and
  d.) mixtures thereof;
and said fabric hueing agent being selected from the group consisting of
  a.) dyes;
  b.) dye-clay conjugates comprising at least one cationic/basic dye and a smectite clay; and
  c.) mixtures thereof.

11. The composition of claim 10, said composition comprising, based on total product weight, from about 0% to about 3% photobleach and/or from about 0.00003% to about 0.3% hueing agent.

12. A method of treating and/or cleaning a surface or fabric comprising the steps of optionally washing and/or rinsing said surface or fabric, contacting said surface or fabric with a composition according to claim 1, then optionally washing and/or rinsing said surface or fabric.

* * * * *

SEQUENCE LISTING

```
<160> NUMBER OF SEQ ID NOS: 6

<210> SEQ ID NO 1
<211> LENGTH: 483
<212> TYPE: PRT
<213> ORGANISM: Bacillus licheniformis

<400> SEQUENCE: 1

Ala Asn Leu Asn Gly Thr Leu Met Gln Tyr Phe Glu Trp Tyr Thr Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
```

-continued

```
                35                  40                  45
Thr Ser Gln Ala Asp Val Gly Tyr Gly Ala Tyr Asp Leu Tyr Asp Leu
 50                  55                  60
Gly Glu Phe His Gln Lys Gly Thr Val Arg Thr Lys Tyr Gly Thr Lys
 65                  70                  75                  80
Gly Glu Leu Gln Ser Ala Ile Lys Ser Leu His Ser Arg Asp Ile Asn
                 85                  90                  95
Val Tyr Gly Asp Val Val Ile Asn His Lys Gly Ala Asp Ala Thr
                100                 105                 110
Glu Asp Val Thr Ala Val Glu Val Asp Pro Ala Asp Arg Asn Arg Val
                115                 120                 125
Ile Ser Gly Glu Tyr Leu Ile Lys Ala Trp Thr His Phe His Phe Pro
130                 135                 140
Gly Arg Gly Ser Thr Tyr Ser Asp Phe Lys Trp His Trp Tyr His Phe
145                 150                 155                 160
Asp Gly Thr Asp Trp Asp Glu Ser Arg Lys Leu Asn Arg Ile Tyr Lys
                165                 170                 175
Phe Gln Gly Lys Ala Trp Asp Trp Glu Val Ser Ser Glu Asn Gly Asn
                180                 185                 190
Tyr Asp Tyr Leu Met Tyr Ala Asp Ile Asp Tyr Asp His Pro Asp Val
                195                 200                 205
Val Ala Glu Ile Lys Arg Trp Gly Thr Trp Tyr Ala Asn Glu Leu Gln
210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Ala Glu Tyr Trp Gln Asn Asp Leu Gly Ala Leu Glu Asn
                260                 265                 270
Tyr Leu Asn Lys Thr Asn Phe Asn His Ser Val Phe Asp Val Pro Leu
                275                 280                 285
His Tyr Gln Phe His Ala Ala Ser Thr Gln Gly Gly Gly Tyr Asp Met
290                 295                 300
Arg Lys Leu Leu Asn Gly Thr Val Val Ser Lys His Pro Leu Lys Ser
305                 310                 315                 320
Val Thr Phe Val Asp Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
                340                 345                 350
Thr Arg Glu Ser Gly Tyr Pro Gln Val Phe Tyr Gly Asp Met Tyr Gly
                355                 360                 365
Thr Lys Gly Asp Ser Gln Arg Glu Ile Pro Ala Leu Lys His Lys Ile
                370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                405                 410                 415
Ser Ser Val Ala Asn Ser Gly Leu Ala Ala Leu Ile Thr Asp Gly Pro
                420                 425                 430
Gly Gly Ala Lys Arg Met Tyr Val Gly Arg Gln Asn Ala Gly Glu Thr
                435                 440                 445
Trp His Asp Ile Thr Gly Asn Arg Ser Glu Pro Val Val Ile Asn Ser
450                 455                 460
```

```
Glu Gly Trp Gly Glu Phe His Val Asn Gly Gly Ser Val Ser Ile Tyr
465                 470                 475                 480

Val Gln Arg
```

<210> SEQ ID NO 2
<211> LENGTH: 269
<212> TYPE: PRT
<213> ORGANISM: Humicola lanuginosa

<400> SEQUENCE: 2

```
Glu Val Ser Gln Asp Leu Phe Asn Gln Phe Asn Leu Phe Ala Gln Tyr
1               5                   10                  15

Ser Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
        50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265
```

<210> SEQ ID NO 3
<211> LENGTH: 485
<212> TYPE: PRT
<213> ORGANISM: Bacillus strain NCIB 12513

<400> SEQUENCE: 3

```
His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30
```

-continued

```
Asn Leu Arg Asn Arg Gly Ile Thr Ala Ile Trp Ile Pro Pro Ala Trp
         35                  40                  45

Lys Gly Thr Ser Gln Asn Asp Val Gly Tyr Gly Ala Tyr Asp Leu Tyr
 50                  55                  60

Asp Leu Gly Glu Phe Asn Gln Lys Gly Thr Val Arg Thr Lys Tyr Gly
 65                  70                  75                  80

Thr Arg Ser Gln Leu Glu Ser Ala Ile His Ala Leu Lys Asn Asn Gly
                 85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
                115                 120                 125

Gln Glu Ile Ser Gly Asp Tyr Thr Ile Glu Ala Trp Thr Lys Phe Asp
            130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
                180                 185                 190

Ser Glu Asn Gly Asn Tyr Asp Tyr Leu Met Tyr Ala Asp Val Asp Met
                195                 200                 205

Asp His Pro Glu Val Val Asn Glu Leu Arg Arg Trp Gly Glu Trp Tyr
            210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
```

-continued

```
            450                 455                 460
Asn Ala Asp Gly Trp Ala Asn Phe Ser Val Asn Gly Gly Ser Val Ser
465                 470                 475                 480

Ile Trp Val Lys Arg
                485

<210> SEQ ID NO 4
<211> LENGTH: 773
<212> TYPE: PRT
<213> ORGANISM: Bacillus sp

<400> SEQUENCE: 4

Ala Glu Gly Asn Thr Arg Glu Asp Asn Phe Lys His Leu Leu Gly Asn
1               5                   10                  15

Asp Asn Val Lys Arg Pro Ser Glu Ala Gly Ala Leu Gln Leu Gln Glu
                20                  25                  30

Val Asp Gly Gln Met Thr Leu Val Asp Gln His Gly Glu Lys Ile Gln
            35                  40                  45

Leu Arg Gly Met Ser Thr His Gly Leu Gln Trp Phe Pro Glu Ile Leu
        50                  55                  60

Asn Asp Asn Ala Tyr Lys Ala Leu Ala Asn Asp Trp Glu Ser Asn Met
65                  70                  75                  80

Ile Arg Leu Ala Met Tyr Val Gly Glu Asn Gly Tyr Ala Ser Asn Pro
                85                  90                  95

Glu Leu Ile Lys Ser Arg Val Ile Lys Gly Ile Asp Leu Ala Ile Glu
            100                 105                 110

Asn Asp Met Tyr Val Ile Val Asp Trp His Val His Ala Pro Gly Asp
        115                 120                 125

Pro Arg Asp Pro Val Tyr Ala Gly Ala Glu Asp Phe Phe Arg Asp Ile
    130                 135                 140

Ala Ala Leu Tyr Pro Asn Asn Pro His Ile Ile Tyr Glu Leu Ala Asn
145                 150                 155                 160

Glu Pro Ser Ser Asn Asn Asn Gly Gly Ala Gly Ile Pro Asn Asn Glu
                165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Val Gly Ser
        195                 200                 205

Pro Asn Trp Ser Gln Arg Pro Asp Leu Ala Ala Asp Asn Pro Ile Asn
    210                 215                 220

Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
                245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Asn Gly Asp Gly Gly Pro
        275                 280                 285

Tyr Phe Asp Glu Ala Asp Val Trp Ile Glu Phe Leu Asn Glu Asn Asn
    290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Asn Leu Asp
                325                 330                 335
```

-continued

```
Pro Gly Pro Asp His Val Trp Ala Pro Glu Leu Ser Leu Ser Gly
            340                 345                 350

Glu Tyr Val Arg Ala Arg Ile Lys Gly Val Asn Tyr Glu Pro Ile Asp
                355                 360                 365

Arg Thr Lys Tyr Thr Lys Val Leu Trp Asp Phe Asn Asp Gly Thr Lys
            370                 375                 380

Gln Gly Phe Gly Val Asn Ser Asp Ser Pro Asn Lys Glu Leu Ile Ala
385                 390                 395                 400

Val Asp Asn Glu Asn Asn Thr Leu Lys Val Ser Gly Leu Asp Val Ser
                405                 410                 415

Asn Asp Val Ser Asp Gly Asn Phe Trp Ala Asn Ala Arg Leu Ser Ala
                420                 425                 430

Asp Gly Trp Gly Lys Ser Val Asp Ile Leu Gly Ala Glu Lys Leu Thr
            435                 440                 445

Met Asp Val Ile Val Asp Glu Pro Thr Thr Val Ala Ile Ala Ala Ile
            450                 455                 460

Pro Gln Ser Ser Lys Ser Gly Trp Ala Asn Pro Glu Arg Ala Val Arg
465                 470                 475                 480

Val Asn Ala Glu Asp Phe Val Gln Gln Thr Asp Gly Lys Tyr Lys Ala
                485                 490                 495

Gly Leu Thr Ile Thr Gly Glu Asp Ala Pro Asn Leu Lys Asn Ile Ala
            500                 505                 510

Phe His Glu Glu Asp Asn Asn Met Asn Asn Ile Ile Leu Phe Val Gly
            515                 520                 525

Thr Asp Ala Ala Asp Val Ile Tyr Leu Asp Asn Ile Lys Val Ile Gly
            530                 535                 540

Thr Glu Val Glu Ile Pro Val Val His Asp Pro Lys Gly Glu Ala Val
545                 550                 555                 560

Leu Pro Ser Val Phe Glu Asp Gly Thr Arg Gln Gly Trp Asp Trp Ala
                565                 570                 575

Gly Glu Ser Gly Val Lys Thr Ala Leu Thr Ile Glu Glu Ala Asn Gly
            580                 585                 590

Ser Asn Ala Leu Ser Trp Glu Phe Gly Tyr Pro Glu Val Lys Pro Ser
            595                 600                 605

Asp Asn Trp Ala Thr Ala Pro Arg Leu Asp Phe Trp Lys Ser Asp Leu
            610                 615                 620

Val Arg Gly Glu Asn Asp Tyr Val Ala Phe Asp Phe Tyr Leu Asp Pro
625                 630                 635                 640

Val Arg Ala Thr Glu Gly Ala Met Asn Ile Asn Leu Val Phe Gln Pro
                645                 650                 655

Pro Thr Asn Gly Tyr Trp Val Gln Ala Pro Lys Thr Tyr Thr Ile Asn
            660                 665                 670

Phe Asp Glu Leu Glu Glu Ala Asn Gln Val Asn Gly Leu Tyr His Tyr
            675                 680                 685

Glu Val Lys Ile Asn Val Arg Asp Ile Thr Asn Ile Gln Asp Asp Thr
            690                 695                 700

Leu Leu Arg Asn Met Met Ile Ile Phe Ala Asp Val Glu Ser Asp Phe
705                 710                 715                 720

Ala Gly Arg Val Phe Val Asp Asn Val Arg Phe Glu Gly Ala Ala Thr
            725                 730                 735

Thr Glu Pro Val Glu Pro Glu Pro Val Asp Pro Gly Glu Glu Thr Pro
            740                 745                 750

Pro Val Asp Glu Lys Glu Ala Lys Lys Glu Gln Lys Glu Ala Glu Lys
```

```
                755                 760                 765
Glu Glu Lys Glu Glu
    770

<210> SEQ ID NO 5
<211> LENGTH: 483
<212> TYPE: PRT
<213> ORGANISM: Bacillus licheniformis

<400> SEQUENCE: 5

Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350
```

```
Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
        370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
            405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
        450                 455                 460

Glu Gly Trp Gly Glu Phe His Val Asn Gly Gly Ser Val Ser Ile Tyr
465                 470                 475                 480

Val Gln Arg

<210> SEQ ID NO 6
<211> LENGTH: 483
<212> TYPE: PRT
<213> ORGANISM: Bacillus licheniformis

<400> SEQUENCE: 6

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240
```

-continued

```
Leu Arg Asp Trp Val Asn His Val Arg Glu Lys Thr Gly Lys Glu Met
                245             250             255

Phe Thr Val Ala Glu Tyr Trp Gln Asn Asp Leu Gly Ala Leu Glu Asn
                260             265             270

Tyr Leu Asn Lys Thr Asn Phe Asn His Ser Val Phe Asp Val Pro Leu
            275             280             285

His Tyr Gln Phe His Ala Ala Ser Thr Gln Gly Gly Tyr Asp Met
        290             295             300

Arg Lys Leu Leu Asn Gly Thr Val Val Ser Lys His Pro Leu Lys Ser
305             310             315             320

Val Thr Phe Val Asp Asn His Asp Thr Gln Pro Gly Gln Ser Leu Glu
                325             330             335

Ser Thr Val Gln Thr Trp Phe Lys Pro Leu Ala Tyr Ala Phe Ile Leu
                340             345             350

Thr Arg Glu Ser Gly Tyr Pro Gln Val Phe Tyr Gly Asp Met Tyr Gly
                355             360             365

Thr Lys Gly Asp Ser Gln Arg Glu Ile Pro Ala Leu Lys His Lys Ile
            370             375             380

Glu Pro Ile Leu Lys Ala Arg Lys Gln Tyr Ala Tyr Gly Ala Gln His
385             390             395             400

Asp Tyr Phe Asp His His Asp Ile Val Gly Trp Thr Arg Glu Gly Asp
                405             410             415

Ser Ser Val Ala Asn Ser Gly Leu Ala Ala Leu Ile Thr Asp Gly Pro
                420             425             430

Gly Gly Ala Lys Arg Met Tyr Val Gly Arg Gln Asn Ala Gly Glu Thr
            435             440             445

Trp His Asp Ile Thr Gly Asn Arg Ser Glu Pro Val Val Ile Asn Ser
        450             455             460

Glu Gly Trp Gly Glu Phe His Val Asn Gly Gly Ser Val Ser Ile Tyr
465             470             475             480

Val Gln Arg
```